United States Patent [19]

Buchwald et al.

[11] Patent Number: 5,576,460
[45] Date of Patent: Nov. 19, 1996

[54] PREPARATION OF ARYLAMINES

[75] Inventors: Stephen L. Buchwald; Anil Guram, both of Somerville, Mass.

[73] Assignee: Massachusetts Institute of Technology, Cambridge, Mass.

[21] Appl. No.: 281,449

[22] Filed: Jul. 27, 1994

[51] Int. Cl.$^6$ ............................................. C07C 209/10
[52] U.S. Cl. ..................... 564/386; 546/144; 560/48; 564/374; 564/376; 564/391; 564/395; 564/405; 564/407
[58] Field of Search ................................. 564/374, 376, 564/386, 391, 395, 405, 407; 560/48; 546/144

[56] References Cited

U.S. PATENT DOCUMENTS

| | | | |
|---|---|---|---|
| 5,233,090 | 8/1993 | Shimada et al. | 564/426 |
| 5,319,009 | 6/1994 | Sasaki et al. | 564/428 X |
| 5,382,692 | 1/1995 | Shimada et al. | 564/426 |
| 5,403,950 | 4/1995 | Shimada et al. | 564/426 X |

OTHER PUBLICATIONS

"Amido-derivatives of Metals and Metalloids. Part IX. Reactions of Tin(IV) and Titanium (IV) Amides with Compounds having Carbonyl and Sulphinyl Multiple Bonds" Chandra et al. *J. Chem. Soc.* (C) 1969, 2565-8 (1969).

"Mechanism and Models for Copper Mediated Nucleophilic Aromatic Substitution. 2. A Single Catalytic Species from Three Different Oxidation States of Copper in an Ullmann Synthesis of Triarylamines" Paine, A. J. *J. Chem Soc.* 109, 1496–1502 (1987).

"Inverse Electron Demand Diels–Alder Reactions of Heterocyclic Aza Dienes. Studies on the Total Synthesis of Lavendamycin: Investigative Studies on the Preparation of the CDE β–Carboline Ring System and AB Quinoline-5, 8–quinone Ring System" Boger et al. *J. Org. Chem.* 50, 5782–5789 (1985).

"Catalytic and Stoichiometric Metal–Mediated C–N Bond-–Forming Processes" Hartwig et al. Paper #235 at the 207th Meeting of the American Chemical Society, Mar. 13–17, 1994, San Diego, California (Abstract only).

"Palladium–Catalyzed Formation of Carbon–Nitrogen Bonds. Reaction Intermediates and Catalyst Improvements in the Hetero Cross–Coupling of Aryl Halides and Tin Amides" Paul et al. *J. Am. Chem. Soc.* 116, 5969–5970 (1994).

"Aromatic Substitution by the $S_{RN}1$ Mechanism" Bunnett, J. F. *Accounts of Chemical Research* 11, 413–420 (1978).

"Studies on nucleophilic substitution reactions with cyclopentadienyliron complexes of some chloroarenes and nitroarenes and syntheses and substituted arenes by demetallation of the substitution products" Abd–El–Aziz et al. *Journal of Organometallic Chemistry* 348, 95–107 (1988).

"Amino–derivatives of Metals and Metalloids. Part I. Preparation of Aminostannanes, Stannylamines, and Stannazanes" Jones, K. and Lappert, M. F. *Journal of the Chemical Society* 1965 1944–1951 (1965).

"Palladium–Catalyzed Aromatic Amination of Aryl Bromides with N,N–Di–Ethylamino–Tributyltin" Kosugi et al. *Chemistry Letters* 1983 927–928 (1983).

"Organic Tin–Nitrogen Compounds" Jones, K. and Lappert, M. F. *Organometallic Chemistry Review* 1, 67–92 (1966).

"Nucleophilic Aromatic Substitution Reactions of 1—Methoxy—2—(diphenylphosphinyl)naphthalene with C—, N—, and O—Nucleophiles: Facile Synthesis of Diphenyl(1–substituted–2—naphythyl)phosphines" Hattori et al. Synthesis 1994 199–202 (Feb. 1994).

*Primary Examiner*—Richard L. Raymond
*Attorney, Agent, or Firm*—Choate, Hall & Stewart

[57] ABSTRACT

A method of preparing an arylamine compound includes reacting a metal amide comprising a metal selected from the group consisting of tin, boron, zinc, magnesium, indium and silicon, with an aromatic compound comprising an activated substituent in the presence of a transition metal catalyst to form an arylamine. The method is useful in preparing mixtures of arylamines for use in screening for pharmaceutical and biological activity and in preparing poly(anilines).

14 Claims, No Drawings

PREPARATION OF ARYLAMINES

This invention was made with government support under Grant Numbers NIH 5R01-GM34917 and NSF CHE-9000482 awarded by the National Institutes of Health and National Science Foundation. The government has certain rights in the invention.

BACKGROUND OF THE INVENTION

The present invention relates to a novel method for preparing arylamines which are useful intermediates and end products in pharmaceutical and agricultural applications. The present invention further relates to applications of the method.

The arylamine moiety is a structural component in a variety of synthetic and naturally occurring biologically active compounds. Methods to construct the carbon-nitrogen bond in arylamines, however, are limited. Many synthetic methods for the construction of such an aryl-nitrogen bond suffer from severe reaction conditions and/or are applicable only for activated substrates. Typical routes to aromatic amines include nucleophilic aromatic substitution of aryl precursors. See, Hattori et al. *Synthesis* 1994, 199 (1994); and Bunnett, J. F. *Acc. Chem. a Res* 1978 11,413 (1978). Synthesis of arylamines via copper-mediated Uhlmann condensation reactions also has been reported. See, Paine, A. J. *J. Am. Chem. Soc.* 1987, 109, 1496 (1987).

Migita and coworkers have described the preparation of N,N-diethylaminobenzenes from the palladium-catalyzed reaction of aryl bromides and N,N-diethylaminotributyltin. See, Kosugi et al. *Chem. Lett.* 1983, 927–928 (1983). However, the general applicability of this synthetic route is limited due to the high reactivity and instability of the aminostannanes (generally, $R_3Sn(NR'_2)$). Jones and Lappert report that many aminostannanes are moisture sensitive, decompose or undergo a condensation reaction to form distannazane compounds (generally, $(R_3Sn)_2NR'$). The high reactivity of aminostannanes may hinder their effective isolation and use in subsequent reactions. See, Jones, K. and Lappert, M. F. *Organomet. Chem. Rev.* 1966 (1), 67–92. Further, the use of aminostannanes is undesirable from an environmental standpoint because of their toxicity.

Boger and coworkers reported the formation of an aryl-nitrogen bond by reaction of an amine moiety with an aryl bromide without the use of a metal amide and, in particular, without the use of an aminostannane. However, the reaction required the use of stoichiometric amounts of palladium(0) in order for the reaction to occur. See, Boger et al. *J. Org. Chem.* 1985 50, 5782.

A general route to a wide range of arylamines under moderate reaction conditions is yet to be reported. Therefore, it is an object of the present invention to provide such a general synthetic route to a wide range of arylamines. It is a further object of the present invention to provide a synthetic route to arylamines which do not require the use of aminostannanes. It is a further object of the present invention to apply the method to obtain useful arylamine derivatives and polymers.

SUMMARY OF THE INVENTION

The present invention provides a general and attractive route to a wide range of arylamines. In one aspect of the present invention, a metal amide is reacted with an aromatic compound having an activated substituent in the presence of a transition metal catalyst to form an arylamine. The metal amide includes a metal selected from the group consisting of boron, zinc, magnesium, indium and silicon.

"Metal amide", as that term is used herein, is meant to include compounds having a metal-amino bond. Such compound also are referred to alternatively as aminometal compounds, such as aminoboranes, aminostannanes, aminosilanes and the like. The metal amide may include additional substituents. In a preferred embodiment, the metal amide has a formula, $(Y)_mM(NR_1R_2)$, where Y is selected from the group consisting of alkyl, acyl, aryl, heteroaryl, hydride, alkoxide, thioalkoxide, amides halide and pseudohalide groups and substituted derivatives thereof, and m is selected to satisfy the valency requirement of the metal. $R_1$ and $R_2$ may be the same or different and are selected from the group consisting of alkyl groups, aromatic groups, cyclic groups such that the free amine is a cyclic amine. In other preferred embodiments, the aromatic compound has a formula, $Ar(Z)_nX$, where Ar is an aryl moiety, where X is an activated substituent, and where Z is selected from the group consisting of alkyl, aryl, heteroaryl, amino, carboxylic ester, carboxylic acid, acyl, hydrogen, ether, thioether, amide, carboxamide, nitro, phosphonic acid, sulphonic acid, halide, pseudohalide groups, and substituted derivatives thereof, and n is in the range of 0 to 5.

In another aspect of the invention, an arylamine is provided by transaminating a first metal amide, the first metal amide comprising a metal (M) selected from the group consisting of tin, boron, zinc, magnesium, indium and silicon, with a first amine to obtain a second metal amide and a second amine. The second metal amide is reacted with an aromatic compound comprising an activated substituent in the presence of a transition metal catalyst to form an arylamine.

In another aspect of the invention, a mixture of arylamines for the screening of pharmaceutical activity is provided by reacting a first metal amide, the metal amide comprising a metal selected from the group consisting of tin, boron, zinc, magnesium, indium and silicon, and a plurality of amines of different composition in a transamination reaction to form a plurality of metal amides of different composition, and thereafter reacting the plurality of metal amides with an aromatic compound comprising an activated substituent in the presence of a transition metal catalyst to form a plurality of arylamines of different composition.

In yet another aspect of the present invention, poly(aniline) is provided by reacting a first metal amide, the metal amide comprising a metal selected from the group consisting of tin, boron, zinc, magnesium, indium and silicon, with a substituted aniline to obtain a metal anilide, and thereafter reacting the substituted metal anilide with a disubstituted aromatic compound, at least one of the substituents being an activated substitute, in the presence of a transition metal catalyst to obtain a poly(aniline).

The method of the present invention provides a simple general route to a wide range of arylamines and to a range of useful mixtures and arylamine products.

DESCRIPTION OF THE PREFERRED EMBODIMENT

The present invention is based upon the discovery that a wide range of metal amides are capable of reacting with aromatic compounds containing an activated substituent to obtain an arylamine. Further, readily available metal amide compounds, in particular, aminostannanes, may be subjected to a transamination reaction to obtain new metal amides which may then be reacted with aromatic compounds having an activated substituent to form arylamines.

The synthetic route used for the preparation of arylamines according to the invention is generally set forth in eq. 1,

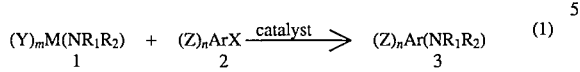  (1)

A metal amide 1 is reacted with an aromatic compound 2 having an activated substituent, X, in the presence of a catalytic amount of transition metal catalyst. The transition metal-catalyzed aromatic amination reaction of eq. 1 most likely proceeds via an initial metal amide-induced reduction of the transition metal catalyst to a zero-valent state, if necessary, followed by an oxidative-addition reaction of the aromatic compound 2 with the metal(0) catalyst, transmetallation and reductive-elimination typical of this class of transition metal catalysts.

Metal amides suitable for use in the present invention include, by way of example only, amides of tin (also known as aminostannanes), boron (also known as aminoboranes), zinc, magnesium, indium and silicon. It is within the scope of the invention for the metal amide to include additional substituents. The metal amide may have the general formula, $(Y)_mM(NR_1R_2)$, where the N-substituents, $R_1$ and $R_2$, may be the same or different. Suitable $R_1$ and $R_2$ include, by way of example only, hydrogen groups, alkyl groups, acyl groups, aromatic and heteroaromatic groups, such substituted phenyl and benzyl and the like, cyclic groups such that the free amine is a cyclic amine, such as piperidine, pyrrolidine and 1,2,3,4-tetrahydroquinoline and the like, and substituted derivatives thereof. The metal amide 1 may include additional substituents, Y. By way of example only, Y may include alkyl, aryl, acyl, heteroaryl, hydride, alkoxide, thioalkoxide, amide, halide, pseudohalide groups, and substituted derivatives thereof, where m is selected to satisfy the valency requirements of the metal. By "substituted derivatives", as that term is used herein, it is meant to include those moieties which have been modified by the addition of substituents that do not significantly affect the properties of that moiety.

Aromatic compound 2 includes compounds derived from simple aromatic rings, heteroaromatic rings, such as pyridine, quinoline, furan, pyrrole, thiophene, and the like, and fused ring systems, such as naphthalene, anthracene, tetralin, imidizole, indole and the like. Suitable aromatic compounds 2, may have the formula $(Z)_nArX$, where X is an activated substituent. An activated substituent, X, is characterized as being a good leaving group which readily lends itself to substitution. For the purposes of the present invention, an activated substituent is that moiety whose conjugate acid, HX, has a pKa of less than 5.0. Suitable activated substituents include, by way of example only, halides such as chloride, bromide and iodide, triflate, mesylate, tosylate, diazonium, and SR, where R=aryl or alkyl. Z is an optional substituent on the aromatic ring. By way of example only, suitable Z include alkyl, aryl, acyl, heteroaryl, amino, carboxylic ester, carboxylic acid, hydrogen group, ether, thioether, amide, carboxamide, nitro, phosphonic acid, sulphonic acid, halide, pseudohalide groups, and substituted derivatives thereof, and n is in the range of 0 to 5. For fused rings, where the number of substitution sites on the aromatic ring increases, n may be adjusted appropriately.

In some instances, it may be necessary to include additional reagents in the reaction to promote reactivity of either the metal amide or the transition metal catalyst. In particular, it may be advantageous to include a base, such as $K_2CO_3$, $Tl_2CO_3$, $CsCO_3$, K(t-BuO), Na(t-BuO), K(OPh), Na(OPh) or mixtures thereof. It is particularly advantageous to include one of K(t-BuO), Na(t-BuO), K(OPh) or Na(OPh) with an additional base, preferably $K_2CO_3$, in reactions using boron amide compounds. In other instances, it may be advantageous to include a quaternary ammonium or silver salts.

In this way a wide range of N-substituted arylamines may be prepared from any available amine. The reaction can be accomplished using a wide range of metal amides, which are either commercially available or obtainable from conventional syntheses using a variety of methods known in the art, such as transamination of metal amides or reaction of the lithium amide with the appropriate metal halide. Interested readers additionally are directed to Niedenzu, K and Dawsen, J. W. "Chemistry of Boron and Its Compounds", E. L. Muetterties, Ed.: J. Wiley & Sons, New York, N.Y., 1967, pp 377–442, which is incorporated herein by reference.

Of particular interest is the transamination reaction. In particular, those metal amides which are not readily available or easily isolated may be made by reaction of an activated aromatic compound with a metal amide generated in situ from the reaction of an first metal amide (prepared according to conventional methods) with a second amine. While particularly advantageous when used with aminostannanes because of their difficulty of preparation and isolation using more conventional routes, the method may be used with any of the metal amide compounds of the present invention.

The synthetic route used for the preparation of arylamines using an in situ-generated metal amide is generally set forth in eq. 2,

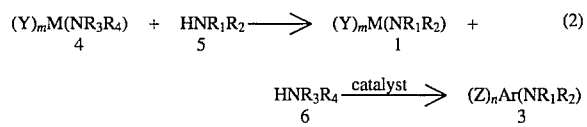  (2)

The starting metal amide 4 may be prepared by any conventional means, typically by reaction of a lithium amide with the appropriate metal halide. The starting metal amide 4 is reacted with a second amine 5 in a transamination reaction. Metal amide 4 reacts with amine 5 to obtain the metal amide 1 with the concomitant formation of amine 6. "Transamination" is used herein in the conventional sense to mean a reaction in which the amino moieties of two compounds of interest are exchanged, so as to form new species containing the exchanged amino groups.

Metal amides 4 suitable for use in the present invention include, by way of example only, amides of tin, boron, zinc, magnesium, indium and silicon. The conventionally prepared amino compounds may include N-substituents, $R_3$ and $R_4$, which may be the same or different. Suitable $R_3$ and $R_4$ include, by way of example only, small chain linear alkyl groups. The metal amide 4 may include additional substituents, Y. By way of example only, Y may include alkyl, aryl, hydride, alkoxide, thioalkoxide, amide, halide, pseudohalide groups, and substituted derivatives thereof, where m is selected to satisfy the valency requirements of the metal. Preferred metal amides 4 include, n-$Bu_3SnN(Et)_2$, $(Et_2N)_3B$, $(Et_2N)_2Zn$, $(Et_2N)_2Mg$, $(Et_2N)_3In$ and $(Et_2N)_4Si$ and comparable $NMe_2$ derivatives thereof.

The amine 5 used in the transamination reaction may be any primary or secondary amine or ammonia. Suitable amines include aliphatic amines, aromatic amines, cyclic amines and acyclic amines and substituted derivatives thereof. The N-substituents, $R_1$ and $R_2$, may be the same or different. Suitable $R_1$ and $R_2$ include, by way of example only, alkyl groups, acyl groups, aromatic and heteroaromatic groups, such substituted phenyl and benzyl and the like, cyclic groups such that the free amine is a cyclic amine, such as piperidine, pyrrolidine and 1,2,3,4-tetrahydroquinoline and the like, and substituted derivatives thereof. Suitable as a first amine may be related compounds such as primary and secondary carboxamides, phosphonamides and substituted derivatives thereof.

It is preferred to remove the amine 6 after or during transamination in order to promote formation of the metal amide 1. Advantageously, the amine 5 is less volatile than the reaction-generated amine 6, thereby facilitating the removal of amine 6 by purging with an inert gas or by reacting under dynamic vacuum. In this way a large number of metal amides may be prepared.

Advantageously, the transamination reaction and the formation of the arylamine are carried out in the same reaction vessel. This avoids the need to isolate and purify the metal amide, which is particularly helpful in those instances where the metal amide is unstable or moisture sensitive. The metal amide 1 is generated in situ by transamination of metal amide 4 and amine 5 and then is reacted with the aromatic compound 2 in the presence of a catalytic amount of transition metal catalyst. In this way a wide range of N-substituted arylamines 3 may be prepared.

The transamination reactions and the aromatic amination reactions take place under mild reaction conditions. Reaction can occur at a temperature in the range of room temperature to 200° C., preferably less than 120° C.

The reactions using metal amides will typically use a near stoichiometric amount of metal amide. However, the reaction may advantageously be accomplished with a catalytic amount of metal amide. In such instances, an amine and an aromatic compound having an activated substituent, X, are reacted in the presence of a catalytic amount of both a metal amide and a transition metal catalyst. The reaction most likely proceeds by the generation of a metal amide from amine, followed by transition metal catalyzed aromatic amination of the aromatic compound to obtain an arylamine. Generation of the arylamine regenerates an active form of the metal to form another metal amide.

In another aspect of the invention, arylamines may be obtained without the use of any metal amides. The general reaction is set forth in eq. 3 and is carried out in the presence of a base, such as potassium or sodium carbonate, triethylamine and the like.

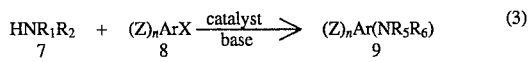

(3)

According to eq. 3, an amide 7 is reacted with an aromatic compound 8 having an activated substituent, X, to form an arylamine 9 in the presence of a catalytic amount of a transition metal catalyst and a base. By way of example only, suitable bases include potassium or sodium carbonate and triethylamine and mixtures thereof. In contrast to the prior art, the reaction requires only catalytic amounts of transition metal catalyst. The aromatic compound 8 and the amine 7 may include any of the moieties listed hereinabove for $R_1$ and $R_2$, Z and X. Preferably the aromatic compound 8 and the amine 7 are included as moieties of a single molecule, whereby the aromatic amination proceeds as an intramolecular process.

Suitable transition metal catalysts for any of the transition metal catalyzed reactions of the present invention include complexes of platinum, palladium, iron, nickel, ruthenium and rhodium. Catalyst complexes may include chelating ligands, such as by way of example only, alkyl and aryl derivatives of phosphines and bisphosphines, imines, arsines, and hybrids thereof, including hybrids of phosphines with amines. Additionally, heterogeneous catalysts containing forms of these elements are also suitable catalysts for any of the transition metal catalyzed reactions of the present invention. Catalysts containing palladium and nickel are preferred. It is expected that these catalysts will perform comparably because they are known to undergo similar reactions, namely oxidative-addition reactions and reductive-elimination reactions, which are thought to be involved in the formation of the arylamines of the present invention.

The active form of the transition metal catalyst is not well characterized. Therefore, it is contemplated that the "transition metal catalyst" of the present invention, as that term is used herein, shall include any transition metal catalyst and/or catalyst precursor as it is introduced into the reaction vessel and which is, if necessary, converted in situ into the active phase, as well as the active form of the catalyst which participates in the reaction. The transition metal catalyst is present in the range of 0.001 to 20 mol %, and preferably 1.0 to 2.5 mol %, with respect to the aromatic compound.

The ease with which the metal amides undergo transamination reactions readily lends itself to the creation of a combinatorial library for the screening of pharmaceutical, agrochemical or other biological or medically-related activity. A combinatorial library for the purposes of the present invention is a mixture of chemically related compounds which may be screened together for a desired biological or agrochemical activity. The preparation of many related compounds in a single reaction greatly reduces and simplifies the number of screening processes which need to be carried out. Screening for the appropriate biological, pharmaceutical and agrochemical activity is done by conventional methods.

A combinatorial library for the screening of pharmaceutical or other related activity may be prepared by reacting in a reaction vessel a first metal amide and a plurality of amines of different composition in a transamination reaction to form a plurality of metal amides comprising the amides of different composition, and thereafter reacting the resulting metal amides with an aromatic compound having an activated substituent in the presence of a transition metal catalyst to form a plurality of arylamines.

Alternatively, a combinatorial library for the screening of pharmaceutical or other related activity may be prepared by reacting in a reaction vessel a metal amide with a plurality of aromatic compounds of different composition, each having an activated substituent, in the presence of a transition metal catalyst to form a plurality of arylamines.

Alternatively, a combinatorial library for the screening of pharmaceutical or other related activity may be prepared by reacting in a reaction vessel a first metal amide and a plurality of amines of different composition in a transamination reaction to form a plurality of metal amides comprising the amides of different composition, and thereafter reacting the resulting metal amides with a plurality of aromatic compounds of different composition, each having an activated substituent, in the presence of a transition metal catalyst to form a plurality of arylamines.

The compositions of the metal amides, amines and aromatic compounds having an activated substituent are comparable to those listed herein above for metal amides 1 and 4, amine 5 and aromatic compound 2.

Further, the method of the present invention for the formation of arylamines may be used in the preparation of polyamines, in particular, poly(anilines). The ready formation of substituted anilines permits the synthesis of poly(aniline) derivatives according to eq. 4.

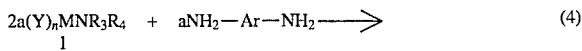

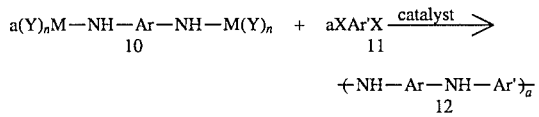

According to eq. 4, a starting amine 1 is reacted with 1,4-diaminobenzene to form the corresponding metal anilide 10. The metal anilide 10 may be further reacted (preferably in situ) with a 1,4-disubstituted aromatic compound 11, where the substituent X is an activated substituent as defined herein, to obtain a poly(aniline) 12. The aryl groups, Ar and Ar', may be the same or different. Suitable aryl groups for Ar and Ar' include aryl groups, a heteroaryl group or substituted groups thereof. The aryl groups may be a substitutional isomer (i.e., para-, meta-, or ortho-substituted). It should be readily apparent that a wide range of substituted poly(anilines) may be obtained by appropriate selection of substituted 1,4-diaminobenzene derivatives for metal amide 10 and/or selection of substituted 1,4-disubstituted aryl derivatives for aromatic compound 11.

Alternatively, a metal anilide 13 including an activated aryl substituent, X, may be used according to the reaction set forth in eq. 5 to obtain poly(anilines).

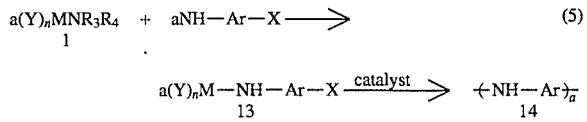

According to eq. 5, a starting amine 1 is reacted with 1-amino,4-X benzene, where the substituent X is an activated substituent as defined herein, to form the corresponding metal anilide 13. The metal anilide 13 reacts (preferably in situ) to obtain a poly(aniline) 12. It should be readily apparent that a wide range of substituted poly(anilines) may be obtained by appropriate selection of substituted aminobenzene derivatives for metal amide 13.

Suitable activated substituents, X, include halides such as chloride, bromide and iodide, triflate, mesylate, tosylate, diazonium, and SR, where R=aryl or alkyl. Metal amides suitable for use in the present invention include, by way of example only, amides of tin (also known as aminostannanes), boron (also known as aminoboranes), zinc, magnesium, indium and silicon. The metal amide 10 may include additional substituents, Y. By way of example only, Y may include alkyl, aryl, hydride, alkoxide, thioalkoxide, amide, halide, pseudohalide groups, and substituted derivatives thereof, where m is selected to satisfy the valency requirements of the metal, as describe herein above.

The invention may be understood with reference to the following examples, which are presented for illustrative purposes only and which are nonlimiting.

EXAMPLE 1

Synthesis of 3-(N-3,4-dimethoxyphenethyl-N-methylamino) anisole. This example illustrates the palladium-catalyzed synthesis of an arylamine by transamination of an aminostannane, followed by aromatic amination.

A solution of 3,4-dimethoxy-N-methylphenethylamine (349 mg, 1.79 mmol) with N,N-diethylaminotributyltin (600 mg, 1.66 mmol) in toluene (2 mL) was heated at 85° C. under argon purge for 1 hr. 3-bromoanisole (221 mg, 1.12 mmol), PdCl$_2$(P(o-tolyl)$_3$)$_2$ (10 mg, 0.02 mmol), and toluene (8 mL) were added. The reaction mixture was heated overnight at ca. 105° C. The reaction mixture was cooled, diluted with ethyl ether (20 mL) and extracted with 4N HCl solution (2×10 mL). The aqueous fraction was cooled to 0° C., made alkaline with 4N NaOH solution (25–30 mL) and extracted with ethyl ether (2×15 mL). The organic fraction was dried with MgSO$_4$, concentrated in vacuo and subjected to column chromatography on silica gel using hexane:ethyl acetate (10:1, 4:1) to afford the title compound as a light pink oil (310 mg, 84%).

EXAMPLES 2–10

Examples 2–10 illustrate the versatility of the method the present invention, in which a transamination reaction is used to prepare a variety of metal amides, which are then reacted in an aromatic amination reaction to form the corresponding arylamine.

A variety of substituted aromatic compounds and substituted amines were subjected to the palladium-catalyzed aromatic amination reaction according to eq. 2 to obtain variously substituted arylamines. The starting aromatic compounds and amines and the corresponding product arylamine are reported in Table 1. The reactions were carried out according to the method described in Example 1, although the reaction times varied somewhat, as discussed hereinbelow. Transamination was accomplished by the reaction of the desired amine with N,N-diethylaminotributyltin; however, it can also be accomplished using N,N-dimethylaminotributyltin. The amines used in Examples 2–10 are all commercially available.

As illustrated in Table 1, the Pd-catalyzed aromatic aminations are fairly general for a variety of in situ generated aminostannanes. Aminostannanes were derived from both aliphatic and aromatic amines including aniline by transamination with N,N-diethylaminotributyltin. The resultant aminostannanes undergo Pd-catalyzed reactions with the listed aryl bromides substituted with either electron-withdrawing or electron-donating substituents to afford the desired arylamine in good yields. In general, aromatic bromides substituted with a para electron donating group substituent reacted slower than those with a para electron withdrawing group (18 h for 4-bromo-N,N-diethylaniline v 1–2 h for ethyl-4-bromobenzoate). Slower reactions were also observed in the case of aminostannanes derived from aniline (30–40 h). However, para-methoxyaniline and N-methylaniline reacted significantly faster (12 h and 8 h, respectively).

TABLE 1

| No. | R" = | Amine | Work-up[a] | Aryl Amine | Yield (%) |
|---|---|---|---|---|---|
| 2 | p-CO$_2$Et | HN(Ph)(Me) | B | EtO$_2$C-C$_6$H$_4$-N(Ph)(Me) | 88 |
| 3 | p-NMe$_2$ | HN(Ph)(Me) | A | Me$_2$N-C$_6$H$_4$-N(Ph)(Me) | 81 |
| 4 | m-Me | HN((CH$_2$)$_{17}$CH$_3$)(Me) | B | m-Me-C$_6$H$_4$-N((CH$_2$)$_{17}$CH$_3$)(Me) | 79 |
| 5 | p-Me | tetrahydroisoquinoline (HN) | A | N-(p-tolyl)-tetrahydroisoquinoline | 55 |
| 6 | m-OMe | HN(CH$_2$CH$_2$Ph)(Me) | A | MeO-C$_6$H$_4$-N(CH$_2$CH$_2$Ph)(Me) | 79 |
| 7 | m-Me | H$_2$N-Ph | B | m-Me-C$_6$H$_4$-NH-Ph | 66 |
| 8 | m-Me | H$_2$N-C$_6$H$_4$-OMe | B | m-Me-C$_6$H$_4$-NH-C$_6$H$_4$-OMe | 64 |
| 9 | p-Me | Me-NH-Ph | B | p-Me-C$_6$H$_4$-N(Me)-Ph | 73 |
| 10 | p-CO$_2$Et | Me-NH-Ph | B | EtO$_2$C-C$_6$H$_4$-N(Me)-Ph | 83 |

[a]Work-up A: the product was extracted with 4N HCl, followed by neutralization of the aqueous fraction with 4N NaOH and extraction with ethyl ether; work-up B: the organics were washed with aqueous KF solution to remove the organostannane as an insoluble n-Bu$_3$Sn—F polymer.

EXAMPLE 11

Synthesis of 3-(N,N-diethylamino)toluene from aromatic iodides.

This example illustrates the use of iodide-substituted aromatic compounds.

Analogous reaction of N,N-diethylaminotributyltin with aromatic iodides were less efficient; however, satisfactory yields (>60% yields of isolated product) could be obtained in the presence of ammonium salts. Thus, the reaction of N,N-diethylaminotributyltin with p-iodotoluene in the presence of N-benzyltriethylammonium chloride in toluene at 100° C. afforded 3-(N,N-diethylamino)toluene in 63% isolated yield.

EXAMPLE 12

Synthesis of 3-(N,N-dimethylamino)anisole using aminoboranes.

This example illustrates the preparation of arylamines from aminoboranes using a homogeneous palladium catalyst with sodium and potassium butoxide and potassium carbonate.

A reaction mixture of tris(N,N-dimethylamino)borane (143 mg, 1.0 mmol), sodium t-butoxide (120 mg, 1.25 mmol), anhydrous potassium carbonate (175 mg, 1.25 mmol) PdCl$_2$(P(o-tolyl)$_3$)$_2$ (11 mg, 0.02 mmol), and 3-bromoanisole (0.12 ml, 0.95 mmol) in toluene (10 mL) was heated at ca. 105° C. under argon purge for ca. 10 h. The reaction mixture was cooled, diluted with ethyl ether (ca. 25 mL), washed with H$_2$O (ca. 15 mL) and then extracted with 4N HCl solution (2×15 mL). The aqueous fraction was cooled to 0° C., made alkaline with 4N NaOH solution (ca. 35 mL) and extracted with ethyl ether (2×25 mL). The organic fraction was dried with MgSO$_4$, concentrated in vacuo and subjected to column chromatography on silica gel using hexane (ca. 75 mL) and then hexane:ethyl acetate (ca. 200 mL) to afford the title compound as a colorless oil (116 mg, 81%).

EXAMPLE 13

Synthesis of 3-(N,N-dimethylamino)anisole using aminoboranes.

This example illustrates the preparation of arylamines from aminoboranes using a heterogeneous palladium catalyst in the presence of phosphine ligand and with potassium or sodium butoxide.

A reaction mixture of tris(N,N-dimethylamino)borane (170 mg, 1.2 mmol), potassium t-butoxide (159 mg, 1.20 mmol), Pd/C (63 mg, 10% on C, 0.06 mmol), P(o-tolyl)$_3$ (35 mg, 0.12 mmol), and 3-bromoanisole (0.12 ml, 0.95 mmol) in toluene (10 mL) was heated at ca. 105° C. under argon purge for ca. 10 h. The title compound was isolated as a colorless oil (114 mg, 80% yield) using the work-up described in Example 12.

EXAMPLE 14

Synthesis of 3-(N,N-dimethylamino)anisole using aminoboranes.

This example illustrates the preparation of arylamines from aminoboranes using a heterogeneous palladium catalyst in the absence of phosphine ligand and with potassium or sodium butoxide and demonstrates that complexing ligands are not necessary for the formation of the active catalytic form.

A reaction mixture of tris(N,N-dimethylamino)borane (103 mg, 0.72 mmol), potassium t-butoxide (97 mg, 0.86 mmol), Pd/C (31 mg, 10% on C, 0.03 mmol), and 3-bromoanisole (0.07 ml, 0.58 mmol) in toluene (10 mL) was heated at ca. 105° C. under argon purge for ca. 10 h. The title compound was isolated as a colorless oil (67 mg, 81% yield) using the work-up described in Example 12.

EXAMPLE 15

Synthesis of N-Benzylindoline.

This example illustrates the preparation of arylamines without the use of a metal amide.

To a suspension of potassium carbonate (276 mg, 0.72 mmol) and tetrakis(triphenylphosphine)palladium(0) (116 mg, 0.1 mmol) in toluene (2.0 mL) was added N-benzyl-o-bromophenethylamine (290 mg, 1.0 mmol) and the reaction was stirred at 100° C. for 40 h. Water (5 mL) and ethyl ether (5 mL) were then added and the reaction mixture was stirred until all solid were dissolved. The layers were separated and the aqueous layer was extracted with ethyl ether (2×5 mL). The combined organic layers were then stirred with 30% hydrogen peroxide (10 mL) for 20 min at room temperature to oxidize the triphenylphosphine. The peroxide layer was separated and the organic layer was washed with water (10 mL). The combined water and peroxide layers were then extracted with ethyl ether (2×20 mL). The combined organic layers were washed successively with saturated aqueous ferrous sulfate and water (10 mL each). The combined ferrous sulfate and water layers were extracted with ethyl ether (2×20 mL). The combined organic layers were washed with saturated sodium chloride and dried over anhydrous magnesium sulfate. Filtration and concentration in vacuo at room temperature afforded 235 mg of a yellow oil. Chromatography of the residue with 40:1 hexane:diethyl ether afforded 158 mg of the title compound as a clear colorless oil (75% yield).

What is claimed is:

1. A method of preparing an arylamine compound, comprising the steps of:

reacting an amine with an aromatic compound comprising an activated substituent at a temperature less than about 120° C. in the presence of a catalyst selected from the group consisting of nickel and palladium catalyst, and a base to form an arylamine, wherein the aromatic compound has a formula, Ar(Z)$_n$X, and Ar is an aryl or heteroaryl moiety, X is an activated substituent selected from the group consisting of chloride, bromide, iodide, triflate, mesylate, tosylate, diazonium, and SR, where R is aryl or alkyl, and Z is selected from the group consisting of alkyl, aryl, heteroaryl, amino, carboxylic ester, carboxylic acid, acyl, hydrogen, ether, thioether, carboxamide, amide, nitro, phosphonic acid, sulphonic acid, halide, pseudohalide groups, and substituted derivatives thereof, and n is in the range of 0 to 5.

2. The method of claim 1, wherein the base is selected from the group consisting of potassium carbonate, sodium carbonate and triethylamine and mixtures thereof.

3. The method of claim 1, wherein the catalyst is a complex or a heterogeneous or supported catalyst.

4. The method of claim 1, wherein the catalyst is present in an amount in the range of 0.001 to 20 mol % with respect to the aromatic compound containing an activated substituent.

5. The method of claim 1, wherein the catalyst is present in an amount in the range of 1 to 2.5 mol % with respect to the aromatic compound containing an activated substituent.

6. The method of claim 1, wherein the catalyst is homogeneous.

7. The method of claim 1, wherein the catalyst is heterogeneous.

8. The method of claim 1, wherein the catalyst is Pd/C.

9. The method of claim 1, wherein the catalyst is PdCl$_2$(P(o-tolyl)$_3$)$_2$.

10. The method of claim 1, wherein the catalyst is tetrakis(triphenylphosphine)pallium(0).

11. The method of claim 1, wherein the base is selected from the group consisting of K$_2$CO$_3$, Tl$_2$CO$_3$, CsCO$_3$, K(t-BuO), Na(t-BuO), K(PhO), K(PhO) and mixtures thereof.

12. The method of claim 1, wherein the amine has a formula, HNR$_1$R$_2$, where R$_1$ and R$_2$ may be the same or different and are selected from the group consisting of alkyl, acyl, hydrogen group, aromatic, heteroaromatic, and cyclic groups such that the free amine is a cyclic amine.

13. The method of claim 1, wherein the amine and aromatic compound are moieties of a single molecule.

14. The method of claim 1, wherein the amine is N-benzyl, N-methyl amine and the aromatic compound is bromo-N,N-dimethylaniline.

* * * * *